US008647648B2

(12) United States Patent
Boyd et al.

(10) Patent No.: US 8,647,648 B2
(45) Date of Patent: *Feb. 11, 2014

(54) COLOR CHANGING CONSUMER PRODUCTS

(75) Inventors: Thomas Boyd, Metuchen, NJ (US); Guisheng Pan, Philadelphia, PA (US); Harsh M. Trivedi, Hillsborough, NJ (US); Wei Wang, East Brunswick, NJ (US); Nora Lin, Basking Ridge, NJ (US)

(73) Assignee: Colgate-Palmolive Company, New York, NY (US)

( * ) Notice: Subject to any disclaimer, the term of this patent is extended or adjusted under 35 U.S.C. 154(b) by 27 days.

This patent is subject to a terminal disclaimer.

(21) Appl. No.: 13/262,513

(22) PCT Filed: Apr. 2, 2009

(86) PCT No.: PCT/US2009/039324
§ 371 (c)(1),
(2), (4) Date: Sep. 30, 2011

(87) PCT Pub. No.: WO2010/114551
PCT Pub. Date: Oct. 7, 2010

(65) Prior Publication Data
US 2012/0070478 A1    Mar. 22, 2012

(51) Int. Cl.
*A61K 8/02* (2006.01)
*A61Q 11/00* (2006.01)
*A61C 15/00* (2006.01)
*C11D 3/02* (2006.01)

(52) U.S. Cl.
USPC .............. 424/401; 424/49; 424/52; 424/58; 433/216; 510/141; 510/218

(58) Field of Classification Search
USPC ......... 424/49, 52, 58, 401; 433/216; 510/141, 510/158, 159, 218, 438
See application file for complete search history.

(56) References Cited

U.S. PATENT DOCUMENTS

| | | | |
|---|---|---|---|
| 3,535,421 A | 10/1970 | Briner et al. | |
| 3,678,154 A | 7/1972 | Widder et al. | |
| 3,696,191 A | 10/1972 | Weeks | |
| 3,937,807 A | 2/1976 | Haefele | |
| 3,959,458 A | 5/1976 | Agricola et al. | |
| 3,991,177 A | 11/1976 | Vidra et al. | |
| 4,051,234 A | 9/1977 | Gieske et al. | |
| 4,058,595 A | 11/1977 | Colodney | |
| 4,150,106 A | 4/1979 | Assal et al. | |
| 4,154,815 A | 5/1979 | Pader | |
| 4,301,141 A | 11/1981 | Scheller | |
| 4,355,022 A | 10/1982 | Rabussay | |
| 4,568,534 A | 2/1986 | Stier et al. | |
| 4,717,710 A | 1/1988 | Shimizu et al. | |
| 4,842,847 A | 6/1989 | Amjad | |
| 4,866,161 A | 9/1989 | Sikes et al. | |
| 4,885,155 A | 12/1989 | Parran, Jr. et al. | |
| 4,992,420 A | 2/1991 | Neeser | |
| 5,000,939 A | 3/1991 | Dring et al. | |
| 5,004,597 A | 4/1991 | Majeti et al. | |
| 5,599,525 A * | 2/1997 | Hsu et al. | 424/49 |
| 5,690,913 A * | 11/1997 | Hsu et al. | 424/53 |
| 6,419,902 B1 | 7/2002 | Wright | |
| 6,669,929 B1 | 12/2003 | Boyd et al. | |
| 6,733,766 B2 | 5/2004 | Gott et al. | |
| 7,053,029 B2 | 5/2006 | MacDonald et al. | |
| 8,119,162 B2 * | 2/2012 | Miksa et al. | 424/489 |
| 8,211,452 B2 * | 7/2012 | Miksa et al. | 424/401 |
| 2003/0124068 A1 | 7/2003 | Atsushi et al. | |
| 2004/0062724 A1 | 4/2004 | Moro et al. | |
| 2004/0134010 A1 | 7/2004 | Tseng et al. | |
| 2005/0106112 A1 | 5/2005 | Boyd et al. | |
| 2006/0246802 A1 * | 11/2006 | Hughes et al. | 442/327 |
| 2007/0148613 A1 | 6/2007 | Stoll | |

FOREIGN PATENT DOCUMENTS

| | | |
|---|---|---|
| FR | 2805162 | 8/2001 |
| JP | S55-153709 | 11/1980 |
| JP | S60-016912 | 1/1985 |
| JP | S63-250314 | 10/1988 |
| JP | 5-178871 | 7/1993 |
| JP | H06-509955 | 11/1994 |
| JP | 2001-278739 | 10/2001 |
| JP | 2009-543900 | 12/2009 |
| WO | WO 96/29047 | 9/1996 |
| WO | WO 2007/008908 | 1/2007 |
| WO | WO 2007/0010553 | 1/2007 |

OTHER PUBLICATIONS

International Search Report and Written Opinion in International Application No. PCT/US09/039324, mailed Nov. 13, 2009.

* cited by examiner

*Primary Examiner* — Blessing M Fubara
(74) *Attorney, Agent, or Firm* — Howard C. Lee

(57) ABSTRACT

The invention relates to personal care products containing multilayer films with decorative layers and may impart a noticeable color change. The invention is applicable in products including type toothpaste, soaps, and other products until diluted with water (or saliva).

27 Claims, No Drawings

… (1)

COLOR CHANGING CONSUMER PRODUCTS

CROSS-REFERENCE TO RELATED APPLICATIONS

The present application is a national stage entry under 35 U.S.C. §371 of International Patent Application No. PCT/US2009/039324, filed Apr. 2, 2009, the entirety of which is hereby incorporated by reference.

BACKGROUND OF THE INVENTION

Sensory signals play an important role in communicating key benefits to the consumer. For example, when using toothpaste there is typically no immediate signal that the product has worked as promised or clone anything during use. A visual cue, such as the foam changing color from white to blue could dramatically improve this perception but the art reports that such technologies may not be currently feasible.

Moreover, a need exists to control the rate at which this color change occurs so that the signal could be used to ensure consumer compliance (e.g., to ensure a child has brushed adequately).

BRIEF SUMMARY OF THE INVENTION

The invention includes a composition that includes a film. The film is composed of a first shielding polymer layer, a middle decorative layer, and a second shielding polymer layer. The first and the second shielding layers obscure at least a portion of the middle decorative layer.

Also included are methods of using the compositions in an oral care, personal care, or home care regimen.

DETAILED DESCRIPTION OF THE INVENTION

As used throughout, ranges are used as a shorthand for describing each and every value that is within the range. Any value within the range can be selected as the terminus of the range. In addition, all references cited herein are hereby incorporated by reference in their entireties, in the event of a conflict in a definition in the present disclosure and that of a cited reference, the present, disclosure controls.

The invention broadly encompasses oral care compositions, personal care compositions, and home care compositions. Oral care compositions include compositions such as toothpaste, personal care compositions include such things as lotions and shower gels, and home care compositions include such things as all-purpose cleaning solutions and dish detergents. Other exemplary compositions are disclosed elsewhere herein.

The invention also encompasses an oral care composition that includes a film. The film includes at least a first and a second shielding polymer layer and a middle-decorative polymer layer that is placed between the first and the second shielding layers. The oral care composition may be in any form, including toothpaste, a gel, a mouthrinse, a lozenge, a floss, a tooth tape, a ship, a confection, or a varnish.

The shielding layers, of which there are at least two, serve to obscure the visual aspect of the decorative layer(s), such that prior to contact with and/or mechanical manipulation in the oral cavity, the true visual aspect of the decorative layer is not apparent. By "obscure" it is intended to include shielding layers which presence over the decorative layer and/or which subsequent absence alters the visual aspect of the film and/or the overall composition. For example, the shielding layers may be opaque and visually shield the decorative layer; the shielding layers may be translucent or transparent but colored, so that the absence of the shielding layer results is a perceived color change of the film; the shielding layers may even be clear, if, the decorative layer contains a component that changes color when exposed to the oral cavity (by removal of the shielding layers), such as a pH or temperature sensitive agent. Alternatively, the shielding layer may be shielding a compound agent in the decorative layer, that, upon release alters an aesthetic of the overall composition, such compound(s) or agents may be visually discernable or not within the decorative layer.

The shielding layers may discontinuous or they may provide coverage for the entire area of the decorative layer. The film may contain more than one decorative layer.

In one embodiment, the shielding layers comprise at least hydroxypropyl methylcellulose (HPMC), glycerin, and titanium oxide. In another embodiment, the shielding layers comprise at least HPMC, glycerin, and titanium oxide. In another embodiment, the middle decorative polymer layers comprise at least HPMC, glycerin, and a pigment. In certain embodiments, a pigment of the decorative middle layer is red, blue, green or mixtures thereof, but any color is suitable. A composition may comprise more than two shielding layers.

In an embodiment, any of the polymer layers may comprise hydroxylpropyl cellulose (HPC). Any of the polymer layers may comprise one or more of a pigment, FD&C color, and lake color, and various color-Imparting compounds, among other things.

The oral care compositions can include various ingredients such as at least one abrasive, at least one fluoride source, at least one agent to increase the amount of foam, at least one surfactant, at least one vitamin, at least one polymer, at least one flavoring agent; at least one enzyme, at least one humectant, and/or at least one preservative and combinations thereof.

The invention also encompasses a method of apprising a user of completion of teeth brushing including applying an oral care composition as described herein comprising a first shielding polymer layer, at least one middle decorative polymer layer, and a second shielding polymer layer, wherein the first and second opaque layers collectively conceal at least a portion of the at least one middle decorative layer to the teeth, brushing the teeth and oral care composition to cause a foam, observing a distinct color change in the oral care composition. In certain embodiments, the color change is in the overall composition or in the foam produced by use of the composition.

For example, when the formulations are used in the normal manner, the film rapidly dissolves, allowing the colorant or pigment to become increasingly prominent. Foam changes color from white to decorative within one minute. This effect can also be illustrated by the change of a 1:3 slurry of toothpaste in water from white to decorative as me toothpaste is distributed and the film dissolves. The degree of color change can be easily changed by increasing or decreasing the quantity of film in the formula.

In certain embodiments, an abrasive is present in the composition in an amount of about 1 to 20 wt %. In certain embodiments, the fluoride source is present in an amount of about 0.01 to 5 wt. %. In certain embodiments, the agent to increase the amount of foam is present in an amount of about 1 to 90 wt. %. In certain embodiments, the flavoring agent in an amount of about 0.01 to 5 wt. %. In certain embodiments, the tape or strip further includes at least one humectant in an amount of about 0.01 to 5 wt. %.

The oral care compositions may further include one or more fluoride ion sources. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference.

Representative fluoride ion sources include, but are not limited to, stannous fluoride, sodium fluoride, potassium fluoride, sodium monofluorophosphate, sodium fluorosilicate, sodium monfluorophosphate (MFP), ammonium fluorosilicate, as well as tin fluorides, such as stannous fluoride and stannous chloride, and combinations thereof. Certain particular embodiments include stannous fluoride or sodium fluoride as well as mixtures thereof.

In certain embodiments, the oral care composition of the invention may also contain a source of fluoride ions or fluorine-providing ingredient in amounts sufficient to supply about 25 ppm to 5,000 ppm of fluoride ions.

Fluoride ion sources may be added to the compositions of the invention at a level of from about 0.01% to 3.0% in one embodiment or from about 0.03% to 1.0%, by weight of the composition in another embodiment.

The oral care compositions of the invention also may include an agent to increase the amount of foam that is produced when the strip or tape adhered to the oral cavity is brushed.

Illustrative examples of agents that increase the amount of foam include, but are not limited to polyoxyethylene and certain polymers including, but not limited to, alginate polymers.

The polyoxyethylene may increase the amount of foam and the thickness of the foam generated by the oral care composition of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be from about 600,000 to about 2,000,000 and in another embodiment from about 800,000 to about 1,000,000. Polyox® is the trade name for the high molecular weight polyoxyethylene produced by Union Carbide.

The polyoxyethylene may be present in an amount from about 1% to 90%, in one embodiment from about 5% to 50% and in another embodiment from about 10% to 20% by weight of the oral care carrier component of the oral care compositions of the present invention.

Another agent optionally included in the oral care tape or strips of the invention is a surfactant or a mixture of compatible surfactants. Suitable surfactants are those which are reasonably stable throughout a wide pH range, for example, anionic, cationic, nonionic or zwitterionic surfactants.

Suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference.

In certain embodiments, the anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate, sodium lauroyl sarcosinate and sodium coconut monoglyceride sulfonates are examples of anionic surfactants of this type. Mixtures of anionic surfactants may also be utilized.

In another embodiment, cationic surfactants useful in the present invention can be broadly defined as derivatives of aliphatic quaternary ammonium compounds having one long alkyl chain containing from about 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof.

Illustrative cationic surfactants are the quaternary ammonium fluorides described in U.S. Pat. No. 3,535,421, to Briner et al, herein incorporated by reference. Certain cationic surfactants can also act as germicides in the compositions.

Illustrative nonionic surfactants mat can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains from about 8 to 18 carbon atoms and one contains an anionic water-solubilizing group, e.g., car boxy, sulfonate, sulfate, phosphate or phosphorate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

The surfactant or mixtures of compatible surfactants can be present in the compositions of the present invention from about 0.1% to about 5.0%, in another embodiment from about 0.3% to about 3.0% and in another embodiment from about 0.5% to about 2.0% by weight of the total composition. The dosage of surfactant in the individual strip or tape (i.e., a single dose) is about 0.001 to 0.05% by weight, 0.003 to 0.03% by weight, and in another embodiment about 0.005 to 0.02% by weight.

Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of about 0.1 to about 5% by weight and about 0.5 to about 1.5% by weight.

The oral care compositions of the invention also may optionally include one or more chelating agents able to complex calcium found in the cell walls of the bacteria. Binding of this calcium weakens the bacterial cell wall and augments bacterial lysis.

Another group of agents suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 1.0% pyrophosphate ions, from about 1.5% to about 6%, from about 3.5% to about 6% of such ions. The dosage chelating agent in the individual ship or tape (i.e., a single dose) is about 0.01 to 0.6% by weight and in another embodiment about 0.035 to 0.06% by weight.

The oral care strips or tape compositions of the invention also optionally include one or more polymers. Such materials are well known in the art, being employed in the form of their free acids or partially or fully neutralized water soluble alkali metal (e.g. potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAP Chemicals Corporation.

Other polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itacontic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such car boxy lie monomers include vlnylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight from 1,000-2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active ammo acids such as aspattic acid, glutamic acid and phosphoserine, as disclosed in U.S. Pat. No. 4,866,161 Sikes et al., incorporated herein by reference.

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. No. 4,992,420; U.S. Pat. No. 4,355,022; U.S. Pat. No. 4,154,815; U.S. Pat. No. 4,058,595; U.S. Pat. No. 3,991,177; and U.S. Pat. No. 3,696,191 all incorporated herein by reference. An enzyme of a mixture of several compatible enzymes in the current invention constitutes from about 0.002% to about 2.0% in one embodiment or from about 0.05% to about 1.5% in another embodiment or in vet another embodiment from about 0.1% to about 0.5%.

Water may also be present in the oral compositions of the invention. Water, employed in the preparation of commercial oral compositions should be deionized and free of organic impurities. Water commonly makes up the balance of the compositions and includes from about 10% to 50%, about 20% to 40% or about 10% to 15% by weight of the oral compositions. This amount of water includes the free water which is added plus that amount which is introduced with other materials such as with sorbitol or any components of the invention.

In preparing oral care compositions, it is sometimes necessary to add some thickening material to provide a desirable consistency. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arable, and gum tragacanth can also be incorporated. Colloidal magnesium aluminum silicate or finely divided silica can be used as component of the thickening composition to further improve the composition's texture. Thickening agents in an amount from 0.5% to 5.0% by weight of the total composition can be used.

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes from about 15% to 70% in one embodiment or from about 30% to 65% in another embodiment by weight of the dentifrice composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

The present invention in its method, aspect involves applying to the oral cavity a safe and effective amount of the compositions described herein. These amounts, for example, from about 20 mm$^2$ to 2000 mm$^2$ of the strip or tape, is kept in the mouth from about 15 seconds to about 12 hours. In addition, the oral, care strip or tape can be left alone to clean the teeth or can be used with a brush.

EXPERIMENTAL EXAMPLES

Example 1

Disintegration Test

In various embodiments, the composition of the present invention passes a disintegration test. In a preferable Disintegration Test, one gram of a composition comprising a sample of film fragments is placed on top of a 2 inch (50.8 mm) magnetic star bar. The stir bar is placed into a transparent vessel, such as s 500 ml beaker containing 300 ml of water at 30° C. The water comprising the stir bar is then, analyzed for the presence of broken and unbroken film fragments. The analysis can include straining the water through a mesh that is less than half an original long dimension of the film shape. This test will show if any pieces did not break up.

Example 2

Color-Change Formula

Examples 2 Illustrates an illustrative embodiment showing the multi-layer color change formula (white→blue).

TABLE 1

Opaque White Layer 1

| Ingredients | Slurry Weight % | Weight % of Solids |
|---|---|---|
| Opaque White Layer 1 | | |
| Water | 71.500 | |
| Methocel HPMC E5 | 10.300 | 36.140 |
| Methocel HPMC E50 | 2.900 | 10.175 |
| $TiO_2$ | 5.800 | 20.351 |
| Propylene Glycol | 9.000 | 31.579 |
| Tween 80 | 0.500 | 1.754 |
| Total | 100.000 | 100.000 |

TABLE 2

Blue Color Layer 2

| Ingredients | Slurry Weight % | Weight % of Solids |
|---|---|---|
| Blue Color Layer 2 | | |
| Water | 71.500 | |
| Methocel HPMC E5 | 10.300 | 36.140 |
| Methocel HPMC E50 | 2.900 | 10.175 |
| Blue pigment | 5.800 | 20.351 |
| Propylene Glycol | 9.000 | 31.579 |
| Tween 80 | 0.500 | 1.754 |
| Total | 100.000 | 100.000 |

TABLE 3

Opaque White Layer 3

| Ingredients | Slurry Weight % | Weight % of Solids |
|---|---|---|
| Opaque White Layer 3 | | |
| Water | 71.500 | |
| Methocel HPMC E5 | 10.300 | 36.140 |
| Methocel HPMC E50 | 2.900 | 10.175 |
| $TiO_2$ | 5.800 | 20.351 |
| Propylene Glycol | 9.000 | 31.579 |
| Tween 80 | 0.500 | 1.754 |
| Total | 100.000 | 100.000 |

Example 3

Preparation of Multi-Layer Color Change Formula of Example 2

Layer 1 was cast 1 mil then dried in a 90° C. oven for 10 minutes. Layer 2 was cast over layer 1 at 1 mil men dried in the same manner. Layer 3 was cast at 3 mil and the final composition dried at 100° C. for another 10 minutes. The films appeared white to off-white. When cut into small pieces and formulated in a toothpaste (formula below).

Example 4

Full Toothpaste with Color Change Film

Examples 4 illustrates an illustrative embodiment showing a full toothpaste of a multi-layer color change formula.

TABLE 4

| Full Toothpaste with color change film | |
|---|---|
| Ingredient | Example 1, Wt. % |
| Polyethylene glycol 600 (PEG-12) | 1.026 |
| $TiO_2$ | 0.001 |
| Sodium CMC | 0.513 |
| Sorbitol | 70.77 |
| Water | 8.682 |
| Sodium saccharin | 0.359 |
| Sodium fluoride | 0.226 |
| Silica abrasive (Zeodent 114) | 8.205 |
| Silica thickener (Zeodent 165) | 8.205 |
| Flavor oil | 0.513 |
| Sodium lauryl sulfate | 0.5 |
| Color Change Film (white-blue-white, triple layer) | 1 |

When the full formulations are used in the normal manner, the film rapidly dissolves, allowing the colorant to become increasingly prominent. In the illustrative example, foam color changes from white to dark blue within one minute. This effect may be illustrated by the change of a 1:3 slurry of toothpaste in water from white to blue as the toothpaste is distributed and the film dissolves. The degree of color change can be easily changed by increasing or decreasing the quantity of film in the formula.

Other colors or effects are easily substituted, by replacing the pigments in the above example:

Example 5

Red Color Change Toothpaste

Replace Blue Pigment in Layer 2 with Iron Oxide or D&C Red #30.

Example 6

Green Color Change Toothpaste

Replace Blue Pigment in Layer 2 with Pigment Green 7.

Example 7

Toothpaste with Delayed Release of Gold Sparkle

Replace blue pigment in Layer 2 with Iron Oxide-based colorants on $TiO_2$-coated mica (available from various manufacturers, such as under the Timeron trade name from Presperse)

Example 8

Toothpaste with Delayed Release of Tingle Sensation

Replace 5% formula glycerin in Layer 2 with Tingle Sensate (from IFF).

Example 9

Blue Color Change/Toothpaste

Replace pigment in the middle layer with take color.

TABLE 5

Components of blue color change dentifrice.

| Ingredients | Slurry Weight % | Weight % of Solids |
|---|---|---|
| An example of blue color layer 2 using FD&C blue No. 1 lake instead of pigment | | |
| Water | 86.1 | |
| Hydroxylpropyl cellulose (HPC) | 4.5 | 32.374 |
| PEG 600 | 2.0 | 14.388 |
| Propylene Glycol | 0.2 | 1.439 |
| Tween 80 | 0.2 | 1.439 |
| FD&C blue No. 1 lake | 7.0 | 50.360 |
| Total | 100.000 | 100.000 |

The color change may be from a white composition to a colored composition. However, it will be understood that the color change may also be from one color to another. In some embodiments, a subsequent color can supplant a previous color. In other embodiments, a subsequent different color may result from combination of a second pigment being combined with a first pigment.

For example, a different colored base, such as a light green base, can be combined with white-blue-white triple layer film in the toothpaste. The color change will be from green to blue.

In another example, instead of the white-colored-white film set forth above, a triple layer film can have one color in the outer layers (i.e., layers 1 and 3), and another color in middle layer. For example, a composition may have a yellow-blue-yellow film scheme. The triple layer film appears yellow, but the resultant foam will change color to blue or green (upon the mixing of the yellow and blue layers).

In other illustrative embodiments alternate film formulations would ensure stability and dissolvability with use. Tuning the dissolving and release could be easily done by increasing the thickness of the respective layers.

A number of references have been cited, the entire disclosures of which are incorporated herein by reference.

What is claimed is:

1. A composition comprising a film, the film comprising:
   a first shielding polymer layer,
   a middle decorative polymer layer, and
   a second shielding polymer layer,
   wherein the first and second shielding layers obscure at least a portion of middle decorative layer and are adapted to reveal the middle decorative layer upon use of the composition; and the composition is in the form of a tooth paste or gel.

2. The composition of claim 1, wherein at least one of the first shielding layer and the second shielding layer of the film are substantially opaque.

3. The composition of claim 1, wherein at least one of the first shielding layer and the second shielding layer of the film are substantially translucent.

4. The composition of claim 1, wherein the film further comprises an inclusion.

5. The composition of claim 4, wherein the inclusion is selected from the group consisting of pearlescent particles, a light reflecting particles, mica, opaque polymer beads, glitter, and flakes.

6. The composition of claim 1, wherein at least one of the first and the second shielding layers dissolves upon exposure to an oral cavity.

7. The composition of claim 1, wherein at least one of the first and the second shielding layers is friable.

8. The composition of claim 1, wherein the film further comprises an additional decorative layer.

9. The composition of claim 8, wherein the decorative layer comprises at least one member selected from the group consisting of a pigment, an FD&C dye, and a lake color.

10. The composition of claim 1, wherein the film further comprises an additional shielding layer.

11. The composition of claim 10, the additional shielding layer comprises at least one member selected from the group consisting of a pigment, an FD&C dye, and a lake color.

12. The composition of claim 1, wherein at least one of the first and second shielding layers further comprises a member selected from the group consisting of titanium oxide, zinc oxide, talc, hectorite, clay, carbon fibers, an opacifying pigment, FD&C, dyes and lake colors.

13. The composition of claim 1, wherein the film contains an active agent.

14. The oral care composition of claim 1, wherein at least one of the polymer layers comprises HPMC and propylene glycol.

15. The oral care composition of claim 1, wherein at least one of the polymer layers comprises hydroxylpropyl cellulose.

16. The composition of claim 1, further comprising at least one abrasive.

17. The composition of claim 16, wherein the abrasive is selected from the group consisting of abrasive silica, sodium metaphosphate, potassium metaphosphate, tricalcium phosphate, dihydrated dicalcium phosphate, aluminum silicate, calcined alumina, bentonite siliceous materials, and combinations thereof.

18. The composition of claim 1, further comprising a member selected from the group consisting of abrasive silica, sodium metaphosphate, potassium metaphosphate, tricalcium phosphate, dihydrated dicalcium phosphate, aluminum silicate, calcined alumina, bentonite, and siliceous materials.

19. The composition of claim 1 further comprising at least one fluoride ion source.

20. The composition of claim 1, further comprising a fluoride ion source selected from the group consisting of sodium fluoride, potassium fluoride, sodium fluorosilicate, sodium monfluorophosphate (MFP), ammonium fluorosilicate, stannous fluoride and stannous chloride.

21. The composition of claim 1 further comprising at least one surfactant.

22. The composition of claim 1 further comprising a compound selected from the group consisting of vitamins, polymers, flavoring agents, enzymes, humectants, preservatives a4 least one vitamin, at least one polymer, at least one flavoring agent; at least one enzyme, at least one humectant, and/or at least one preservative and combinations thereof.

23. The composition of claim 1, further comprising sodium alginate or polyoxyethylene.

24. The composition of claim 1, further comprising an agent selected from the group consisting of oil of wintergreen, oil of peppermint, oil of spearmint, oil of sassafras, oil of clove, aspartame, acesulfame, saccharin, dextrose, levulose and sodium cyclamate.

25. A method of removing plaque from the surfaces of the oral cavity comprising contacting a surface of the oral cavity with the composition of claim 1 and mechanically manipulating the composition against the surface of the oral cavity until at least one of the first and the second shielding layers of the film are removed and at least a portion of the decorative layer is revealed.

26. The method of claim 25, wherein mechanical manipulation is accomplished by an action selected from the group consisting of mastication, flossing, toothbrushing, rubbing, wiping, and rinsing.

27. The method of claim 25, wherein the revelation of the decorative layer is indicated by a change in color of the entire composition.

* * * * *